United States Patent
Sattler et al.

(10) Patent No.: US 10,858,298 B2
(45) Date of Patent: Dec. 8, 2020

(54) PREPARATION OF DIPHENYL COMPOUNDS

(71) Applicant: ExxonMobil Research and Engineering Company, Annandale, NJ (US)

(72) Inventors: Aaron Sattler, Annandale, NJ (US); Victor DeFlorio, Newton, NJ (US); Michele L. Paccagnini, Randolph, NJ (US); Allen W. Burton, Stewartsville, NJ (US)

(73) Assignee: ExxonMobil Research and Engineering Company, Annadale, NJ (US)

( * ) Notice: Subject to any disclaimer, the term of this patent is extended or adjusted under 35 U.S.C. 154(b) by 33 days.

(21) Appl. No.: 16/366,074

(22) Filed: Mar. 27, 2019

(65) Prior Publication Data

US 2019/0315665 A1    Oct. 17, 2019

Related U.S. Application Data

(60) Provisional application No. 62/656,516, filed on Apr. 12, 2018.

(51) Int. Cl.
  *C07C 1/24* (2006.01)
  *C07C 15/14* (2006.01)
  *C07C 5/367* (2006.01)

(52) U.S. Cl.
  CPC .............. *C07C 1/24* (2013.01); *C07C 5/367* (2013.01); *C07C 15/14* (2013.01)

(58) Field of Classification Search
  CPC ....... C07C 51/353; C07C 15/14; C07C 5/367; C07C 2/74; C07C 45/70; C07C 67/343; C07C 67/347; C07C 69/76; C07C 13/28; C07C 69/82; C07C 1/247; C07C 2601/14; C07C 29/32; C07C 2/865; C07C 6/04; C07C 15/08; C07C 33/26; C07C 47/542; C07C 47/56; C07C 63/04; B01J 2229/183; B01J 2229/20; B01J 2229/42; B01J 23/6527; B01J 29/0341; B01J 29/035; B01J 29/047; B01J 29/126; B01J 29/405; B01J 29/7057; B01J 29/7415; B01J 29/7476; B01J 29/89
  See application file for complete search history.

(56) References Cited

U.S. PATENT DOCUMENTS

| | | |
|---|---|---|
| 3,626,020 A | 12/1971 | Neuzil |
| 3,699,182 A | 10/1972 | Cattanach |
| 6,730,625 B1 | 5/2004 | Chang et al. |
| 8,580,120 B2 | 11/2013 | Porter |
| 9,085,669 B2 | 7/2015 | Dakka et al. |
| 9,328,053 B2 | 5/2016 | Bai et al. |
| 9,580,572 B2 | 2/2017 | Dakka et al. |
| 9,663,417 B2 | 5/2017 | Dakka et al. |
| 9,688,602 B2 | 6/2017 | Dakka et al. |
| 9,896,393 B2 | 2/2018 | Salciccioli et al. |
| 2009/0326310 A1 | 12/2009 | Kulprathipanja et al. |
| 2014/0364631 A1* | 12/2014 | Davis .................. C07C 67/343 549/463 |
| 2016/0176785 A1 | 6/2016 | Salciccioli et al. |

FOREIGN PATENT DOCUMENTS

| | | |
|---|---|---|
| WO | 2014117076 A1 | 7/2014 |
| WO | 2014117076 A9 | 7/2015 |
| WO | 2015112252 A1 | 7/2015 |
| WO | 20150191289 A1 | 12/2015 |

OTHER PUBLICATIONS

Baertsch et al., "Permeation of aromatic hydrocarbon vapors through silicalite-zeolite membranes", J. Phys. Chem, 1996, vol. 100, pp. 7676-7679.
Foster et al., "A geometric solution to the largest-free-sphere problem in zeolite frameworks", Micropo. Mesopor. Mat., 2006, vol. 90, pp. 32-38.
Funke et al., "Separation of close-boiling hydrocarbons with silicalite zeolite", J. Chem. Soc. Faraday Trans., 1996, vol. 92, pp. 2499-2502.
Minceva et al., "Modeling and simulation of a simulated moving bed for the separation of p-xylene", Ind. Eng. Chem. Res., 2002, vol. 41, pp. 3454-3461.
Minceva et al., "Understanding and revamping of industrial scale SMB units for p-xylene separation", AIChE Journal, 2007, vol. 53, pp. 138-149.
Pais et al., "Chiral separation by SMB chromatography", Sep. Pur. Tech., 2000, vol. 20, pp. 67-77.
Rajendran et al., "Simulated moving bed chromatography for the separation of enantiomers", J. Chrom. A, 2009, vol. 1216, pp. 709-738.

(Continued)

*Primary Examiner* — Sharon Pregler
(74) *Attorney, Agent, or Firm* — Priya G. Prasad

(57) ABSTRACT

This disclosure relates to the preparation of diphenyl compounds, especially dimethylbiphenyl compounds, in which there is one methyl group on each ring, and their oxidized analogues. These compounds, and particularly alkylated biphenyl compounds and biphenylcarboxylic acids, alcohols and esters, are useful intermediates in the production of a variety of commercially valuable products, including polyesters and plasticizers for PVC and other polymer compositions.

23 Claims, No Drawings

(56) References Cited

OTHER PUBLICATIONS

Silva et al., "Fixed-bed adsorption of aromatic C8 isomers: Breakthrough experiments, modeling and simulation", 2012, vol. 90, pp. 246-256.
Silva et al., "Modeling and simulation of an industrial-scale parex process", AIChE Journal, 2015, vol. 61, pp. 1345-1363.
Tokay et al., "Nanoparticle silicalite-1 crystallization from clear solutions: Nucleation", Micropor. Mesopor. Mat., 2009, vol. 118, pp. 143-151.
Ruthven et al., "Counter-Current and Simulated Counter-Current Adsorption Separation Processes", Chem. Eng. Sci., 1989, vol. 44, pp. 1011-1038.

* cited by examiner

PREPARATION OF DIPHENYL COMPOUNDS

CROSS-REFERENCE TO RELATED APPLICATIONS

This application claims priority to U.S. Provisional Application Ser. No. 62/656,516 filed Apr. 12, 2018, which is herein incorporated by reference in its entirety

FIELD

This disclosure relates to the preparation of diphenyl compounds, especially dimethylbiphenyl compounds, in which there is one methyl group on each ring, and their oxidized analogues.

BACKGROUND

Biphenyl compounds, and particularly alkylated biphenyl compounds and biphenylcarboxylic acids, alcohols and esters are useful intermediates in the production of a variety of commercially valuable products, including polyesters and plasticizers for PVC and other polymer compositions. For example, biphenyl mono- and dicarboxylic acids can be converted to plasticizers by esterification with long chain alcohols. In addition, diphenyl dicarboxylic acids are potential precursors, either alone or as a modifier for polyethylene terephthalate (PET), in the production of polyester fibers, engineering plastics, liquid crystal polymers for electronic and mechanical devices, and films with high heat resistance and strength. The 4-monocarboxylic acid and the 4,4'-dicarboxylic acid isomers are the most desired due to the properties of the resulting products and hence they have the broadest broadly application.

As disclosed in U.S. Pat. Nos. 9,580,572 and 9,663,417, the entire disclosures of which are incorporated herein by reference in their entirety, biphenyl carboxylic acids can be prepared by oxidation of dimethylbiphenyl (DMBP) compounds, which in turn may be produced by hydroalkylation of toluene followed by dehydrogenation of the resulting (methylcyclohexyl)toluene (MCHT). However, the DMBP product comprises a mixture of all six DMBP isomers, namely 2,2',2,3' 2,4',3,3',3,4' and 4,4' DMBP, in which the 3,4' isomer is usually the most abundant and the 4,4' isomer normally comprises less than 20% of the overall isomer mixture. Thus, to maximize the production of the preferred 4,4' isomer, most of the product must be recycled to an isomerization reactor, which increases the cost and complexity of the process.

Alternative routes to DMBP compounds via benzene are described in U.S. Pat. No. 9,085,669, in which the benzene is initially converted to biphenyl, either by oxidative coupling or by hydroalkylation to cyclohexyl benzene (CHB) followed by dehydrogenation of the CHB, and then the biphenyl is alkylated with methanol. Again, the alkylated product comprises a mixture of DMBP isomers in which the 4,4' isomer is a minor component.

There is interest in developing alternative processes for producing diphenyl compounds and especially dimethylbiphenyl compounds and their oxidized analogues, in which the concentration of the 4,4'-isomers can be increased.

SUMMARY

According to the present disclosure, it has now been found that diphenyl compounds, including 4,4' dimethylbiphenyl and the corresponding alcohols, aldehydes, acids and esters, can be formed by a process including a Diels-Alder type cycloaddition reaction between styrene and/or a substituted styrene and furan and/or a substituted furanyl compound. Similar results can be obtained starting from vinylcyclohexane, vinylcyclohexene and their substituted analogs followed by dehydrogenation of the resultant cyclohexylphenyl or cyclohexenylphenyl compound. Further, depending on the conditions and/or catalyst employed, the reaction can produce a close analogue of a biphenyl by addition to produce, for example, a 1,1-phenyl-furyl-ethane which can then undergo a separate Diels-Alder/dehydration reaction with ethylene to produce a 1,1-diphenyl ethane compound.

Thus in one aspect, the present disclosure provides a process for producing a biphenyl compound, the process comprising:

(a1) reacting furan or a substituted furan compound having the formula (I):

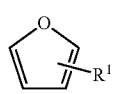

where $R^1$ is —H, —$CH_3$, —CHO, —$CH_2OH$, —COOH or —$COOR^2$ and $R^2$ is an alkyl group having from 1 to 20 carbon atoms with a compound having the formula (II):

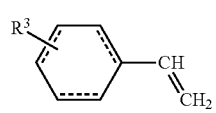

where $R^3$ is —H, —$NO_2$, —$CH_3$, —CHO, —$CH_2OH$, —COOH or —$COOR^4$ and $R^4$ is an alkyl group having from 1 to 20 carbon atoms under cycloaddition conditions effective to produce a compound having the formula (III):

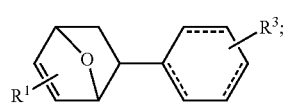

and (b1) dehydrating the compound of formula (III) to produce a compound of formula (IV):

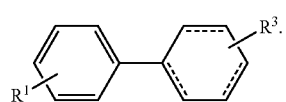

In another aspect, the present disclosure provides a process for producing a close analogue of a biphenyl, referred to herein as a diphenyl compound, the process comprising:

(a2) reacting furan or a substituted furan compound having the formula (I):

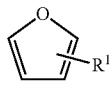

where $R^1$ is —H, —$CH_3$, —CHO, —$CH_2OH$, —COOH or —$COOR^2$ and $R^2$ is an alkyl group having from 1 to 20 carbon atoms with a compound having the formula (II):

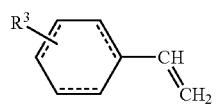

where $R^3$ is —H, —$NO_2$, —$CH_3$, —CHO, —$CH_2OH$, —COOH or —$COOR^4$ and $R^4$ is an alkyl group having from 1 to 20 carbon atoms under alkylation conditions effective to produce a compound having the formula (V):

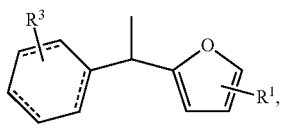

(b2) reacting at least part of the compound of formula (V) with ethylene under cycloaddition reaction conditions to produce a compound having the formula (VI):

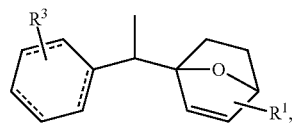

and (c2) dehydrating the compound of formula (VI) to produce a compound of formula (VII):

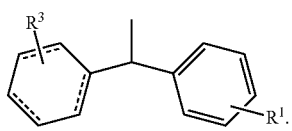

In a further aspect, the present disclosure provides a product composition comprising a mixture of the compound of formula (IV) and the compound of formula (I) and/or the compound of formula (II).

In yet a further aspect, the present disclosure provides a product composition comprising a mixture of the compound of formula (VII) and one or more of the compounds of formula (I), formula (II) and formula (V).

DETAILED DESCRIPTION OF THE EMBODIMENTS

As used herein, the term "diphenyl compound" means any compound having two separate phenyl rings on the same molecule, whereas the term "biphenyl compound" means any diphenyl compound in which a carbon atom of one phenyl ring is directly bonded to a carbon atom of the other phenyl ring.

In addition, it is to be appreciated that the dashed lines in the structural formula of compound (II) and the reaction products thereof designate optional double bonds so that compound (II), for example, may be a substituted or unsubstituted styrene, vinylcyclohexane or vinylcyclohexene.

Described herein is a novel process for producing diphenyl compounds, and especially dimethylbiphenyl compounds and their corresponding alcohols, acids and esters, by reaction of furanyl compounds with styrenyl, vinylcyclohexanyl and/or vinylcyclohexenyl compounds by either cycloaddition or alkylation.

In a first aspect, the process comprises reacting furan or a substituted furan compound having the formula (I):

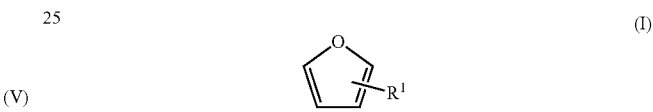

where $R^1$ is —H, —$CH_3$, —CHO, —$CH_2OH$, —COOH or —$COOR^2$ and $R^2$ is an alkyl group having from 1 to 20 carbon atoms with a compound having the formula (II):

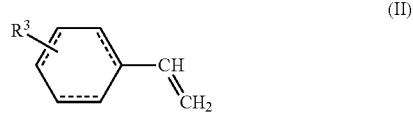

where $R^3$ is —H, —$NO_2$, —$CH_3$, —CHO, —$CH_2OH$, —COOH or —$COOR^4$ and $R^4$ is an alkyl group having from 1 to 20 carbon atoms under cycloaddition conditions effective to produce a compound having the formula (III):

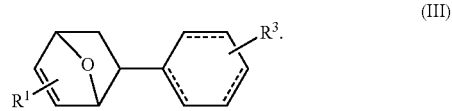

The compound (III) then undergoes dehydration, normally in-situ in the cycloaddition reaction zone, to produce a bicyclic compound of formula (IV):

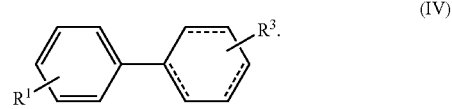

In one embodiment of this first process aspect, the vinyl-group-containing compound (II) comprises vinylcyclohexane or vinylcyclohexene or a substituted variant thereof. The bicyclic product of formula (IV) is then a phenylcyclohexane or a phenylcyclohexene, which can readily be dehydrogenated to produce a biphenyl compound. The dehydrogenation is conveniently conducted at a temperature from about 200° C. to about 600° C. and a pressure from about 100 kPa to about 350 kPa (atmospheric to about 50 psig) in the presence of dehydrogenation catalyst. A suitable dehydrogenation catalyst comprises one or more elements or compounds thereof selected from Group 10 of the Periodic Table of Elements, for example platinum, on a support, such as silica, alumina or carbon nanotubes. In one embodiment, the Group 10 element is present in an amount from about 0.1 to about 5 wt % of the catalyst. In some cases, the dehydrogenation catalyst may also include tin or a tin compound to improve the selectivity to the desired methyl-substituted biphenyl product. In one embodiment, the tin is present in an amount from about 0.05 to about 2.5 wt % of the catalyst.

In another embodiment of this first process aspect, the vinyl-group-containing compound (II) comprises styrene or a substituted styrene and the bicyclic product of formula (IV) is a biphenyl compound. In a preferred embodiment of this process aspect, the starting furan compound of formula (I) has the $R^1$ group in the 3-position relative the ring oxygen atom and the starting styrene compound has the $R^3$ group in the 4- or para-position relative to the vinyl group since the cycloaddition and dehydration sequence then yields the desirable 3,4'- and 4,4'-dimethylbiphenyl isomers according to the following reactions:

Para-methyl styrene is readily available but the most abundant furan compounds have substitution in the 2- and the 2,5-positions since, for example, furfural can be produced from renewable sources, such as hemi-cellulose. In the case of the Diels-Alder/dehydration sequence with para-methyl styrene and 2-methylfuran, the products include 3,4'-dimethylbiphenyl and the less desirable 2,4'-isomer according to the following reactions:

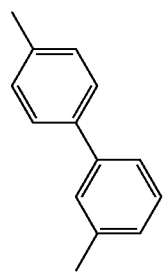
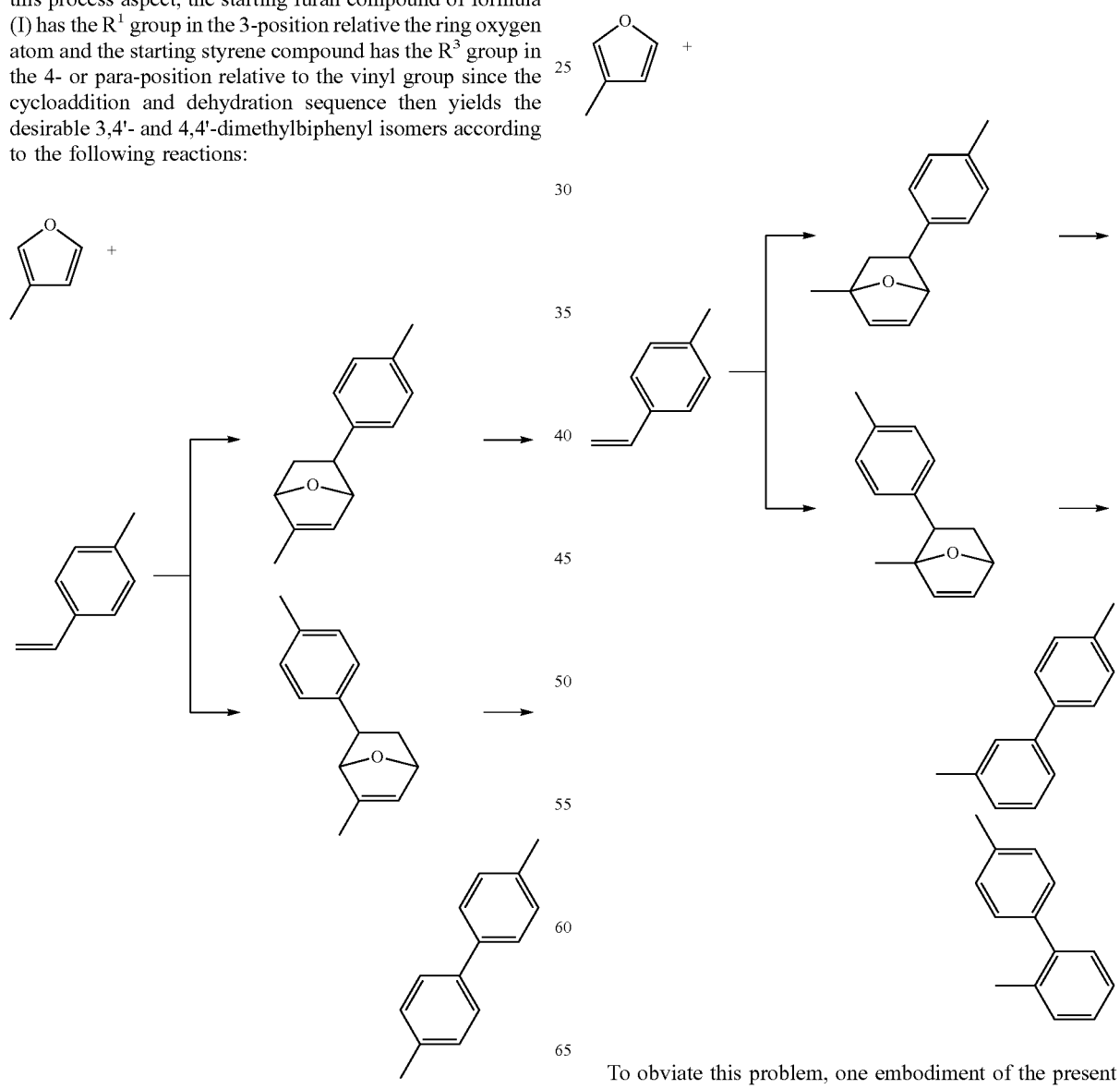

To obviate this problem, one embodiment of the present process includes the step of isomerizing 2-methylfuran to an equilibrium mixture of 2- and 3-methylfuran, from which the 3-isomer could be recovered. A suitable method of isomerizing 2-methylfuran comprises contacting the 2-methylfuran with an acid catalyst, especially a solid acid catalyst, at a temperature of from about 100 to about 250° C.

Additionally or alternatively, it is known from, for example, U.S. Patent Application Publication No. 2016/176785, the entire contents of which are incorporated herein by reference, that 2,X'-(where X' is 2, 3 or 4) dimethylbiphenyl compounds can be isomerized into an equilibrium mixture of dimethylbiphenyl isomers, including the desirable 4,4'-isomer, by contact at elevated temperature with a solid acid catalyst. Similarly, it is known from, for example, U.S. Patent Application Publication No. 2015/361011, the entire contents of which are incorporated herein by reference, that 2,X'-dimethylbiphenyl (DMBP) compounds can be converted to a DMBP isomer mixture with an increased concentration of the 4,4' isomer by a three step process comprising (i) hydrogenation to methylcyclohexyltoluene (MCHT), followed by (ii) transalkylation of the MCHT and then (iii) dehydrogenation back to DMBP.

The cycloaddition/dehydration reaction between compounds (I) and (II) may be conducted with or without a Diels-Alder catalyst, which may be a heterogeneous solid acid catalyst or a homogeneous acid system. Suitable catalysts are Lewis acids (e.g. $ZnCl_2$, $ZnI_2$, $Et_2AlCl$), acidic molecular sieves, such as MFI, BEA, MOR, FAU and MWW structure type molecular sieves (e.g. zeolite Y, Sn-BEA, Zr-BEA), $Cu(BF_4)_2$ and hydroquinone (polymerization inhibitor), and $LiClO_4$. Suitable conditions for the cycloaddition/dehydration reaction include a temperature from about 100° C. to about 400° C., and a pressure of 25 to 5000 psig (170 to 34500 kPa-a), with higher pressures (such as, greater than 540 psig) being preferred because of the high negative entropy of activation. The cycloaddition reaction is further favored by the inclusion of an electron-withdrawing group, such as $NO_2$, as a substituent $R_3$ on the vinyl-group-containing compound (II).

The cycloaddition reaction can be conveniently conducted in the presence of an organic solvent, such as toluene, cyclohexane, or dioxane, or conducted without solvent. The combination of the cycloaddition reaction and the dehydration reaction can be conducted in the same reaction zone in the presence of the same catalyst, or two catalysts.

In some embodiments, it will be appreciated that the initial product recovered from the combined cycloaddition and dehydration sequence will be a mixture of the compound of formula (IV) together with some unreacted compound of formula (I) and/or unreacted compound of formula (II). In addition, the initial product may include by-products of competing reactions, such as linear addition or alkylation of the furan compound (I) by the vinyl group of the compound (II). This alternative reaction sequence will be discussed in more detail below.

Thus, in a second aspect, the present process comprises reacting furan or a substituted furan compound having the formula (I):

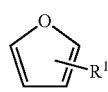
(I)

where $R^1$ is —H, —$CH_3$, —CHO, —$CH_2OH$, —COOH or —$COOR^2$ and $R^2$ is an alkyl group having from 1 to 20 carbon atoms with a vinyl group-containing compound having the formula (II):

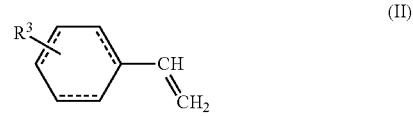
(II)

where $R^3$ is —H, —$NO_2$, —$CH_3$, —CHO, —$CH_2OH$, —COOH or —$COOR^4$ and $R^4$ is an alkyl group having from 1 to 20 carbon atoms under linear addition or alkylation conditions effective to produce a compound having the formula (V):

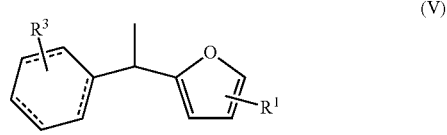
(V)

Suitable alkylation catalysts and conditions overlap those identified above for the cycloaddition/dehydration reaction, although lower pressures, such as from about 170 to 540 kPa-a, may favor alkylation over cycloaddition. Also certain acidic molecular sieve catalysts, such as Sn-BEA, also favor alkylation rather than cycloaddition.

The compound of formula (V) is then reacted with ethylene under cycloaddition reaction conditions to produce a compound having the formula (VI):

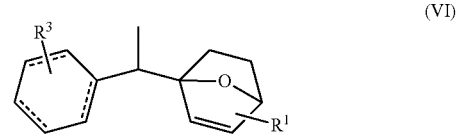
(VI)

which then can undergo dehydration to produce a compound of formula (VII):

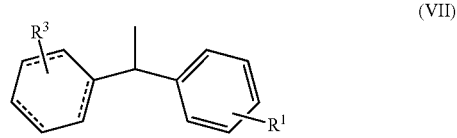
(VII)

Suitable conditions for the ethylene cycloaddition reaction include a temperature from about 100° C. to about 400° C. and a pressure of from about 25 to 5000 psig (about 170 to 34500 kPa-a). The reaction may be conducted in the presence of a catalyst. Suitable catalysts comprise acidic molecular sieves, such as MFI, BEA, MOR, FAU and MWW structure type molecular sieves. In other embodiments, homogeneous Lewis acid-based systems, such as $AlCl_3$ and $Ti(OR^4)_4$, where $R^4$ comprises an alkyl group having from 1 to 4 carbon atoms can be used as the catalyst.

In one embodiment of this second process aspect, the vinyl-group-containing compound (II) comprises vinylcyclohexane or vinylcyclohexene or a substituted variant thereof The bicyclic product of formula (VII) is then a 1-phenyl-1-cyclohexyl ethane or a 1-phenyl-1-cyclohexenyl ethane, which can readily be dehydrogenated to produce a diphenyl compound. The dehydrogenation can be carried out using the same conditions and catalysts as discussed above for the product of formula (IV).

In another embodiment of this second process aspect, the vinyl-group-containing compound (II) comprises styrene or a substituted styrene and the bicyclic product of formula (VII) is a 1,1-diphenyl ethane compound.

Where $R^1$ in the starting furanyl compound (I) and/or $R^3$ in the starting styrenyl compound (II) is —$CH_3$, —CHO, or —$CH_2OH$, the compound (IV) or the compound (VII) can be oxidized to the corresponding carboxylic acid by methods well known in the art, for example by reaction with an oxidant, such as oxygen, ozone or air, or any other oxygen source, such as hydrogen peroxide, in the presence of a catalyst and with or without a promoter, such as Br, at temperatures from 30° C. to 300° C., such as from 60° C. to 200° C. Suitable catalysts comprise Co or Mn or a combination of both metals. The oxidation is normally conducted in solution, generally in acetic acid as solvent.

It will be appreciated that the compound of formula (IV) or the compound (VII), where $R^1$ and/or $R^3$ is —COOH, can be converted to an ester by reaction with an alcohol. Similarly, the compound of formula (IV) or the compound (VII), where $R^1$ and/or $R^3$ is —$CH_2OH$, can be esterified by reaction with a carboxylic acid.

The invention will now be more particularly described with reference to the following non-limiting Examples.

Examples 1 to 3

Table 1 summarizes a series of tests that were conducted to investigate the Diels Alder reaction between 2-methylfuran as the diene and 4-methylstyrene and vinylcyclohexane as the dienophile. In each case the reaction was conducted at an initial pressure of 500 psig, which then increased in pressure autogeneously with increased temperature, in the presence of dioxane as a solvent and without a catalyst. The products were analyzed by mass spectroscopy. The parent masses of the Diels-Alder adducts were observed in all three cases, which indicated that the two molecules were coupling together to form the large molecular weight product. Furthermore, all three products showed similar fragmentation patterns, which would be expected because all contain the oxabicyclo[2.2.1]hept-2-ene moiety.

TABLE 1

| Ex. | Diene | Dienophile | Solvent | Temp. (° C.) | Pressure at Temp. (psig) |
|---|---|---|---|---|---|
| 1 | 2-Methylfuran | 4-Methylstyrene | Dioxane | 120 | 694 |
| 2 | 2-Methylfuran | 4-Methylstyrene | Dioxane | 225 | 952 |
| 3 | 2-Methylfuran | Vinylcyclohexane | Dioxane | 200 | 830 |

Example 4

In this Example, styrene was reacted with furan at 100° C. and atmospheric pressure in the presence of Sn-BEA as a catalyst and toluene as a solvent. The product was characterized by NMR spectroscopy and mass spectrometry. The most notable chemical shifts in the NMR spectrum were that at 1.43 and 3.91 ppm, which are the methyl (CH—$CH_3$) and methine (CH—$CH_3$) hydrogens, respectively. This is consistent with the product containing 1,1-phenyl-furyl-ethane.

In addition, the mass spectra of the product showed disparate fragmentation patterns, indicating this product is not the Diels-Alder addition with the oxabicyclo[2.2.1]hept-2-ene moiety.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention. All documents described herein are incorporated by reference herein, including any priority documents and/or testing procedures to the extent they are not inconsistent with this text. Likewise, the term "comprising" is considered synonymous with the term "including" for purposes of Australian law and whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa.

The invention claimed is:

1. A process for producing a biphenyl compound, the process comprising:
   (a1) reacting furan or a substituted furan compound having the formula (I):

(I)

where $R^1$ is —H, —$CH_3$, —CHO, —$CH_2OH$, —COOH or —$COOR^2$ and $R^2$ is an alkyl group having from 1 to 20 carbon atoms with a compound having the formula (II)

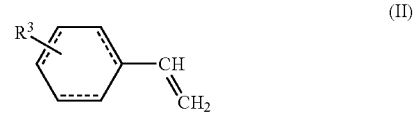

(II)

where $R^3$ is —H, —$NO_2$, —$CH_3$, —CHO, —$CH_2OH$, —COOH or —$COOR^4$ and $R^4$ is an alkyl group having from 1 to 20 carbon atoms under cycloaddition conditions effective to produce a compound having the formula (III):

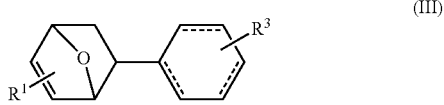

(III)

and
   (b1) dehydrating the compound of formula (III) to produce a compound of formula (IV):

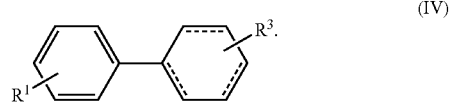

(IV)

2. The process of claim 1, wherein the reacting step (a1) is conducted in the presence of a catalyst.

3. The process of claim 2, wherein the catalyst comprises an acidic molecular sieve or a Lewis acid.

4. The process of claim 1, wherein the conditions in (a1) include a temperature from about 100° C. to about 400° C.

5. The process of claim 1, wherein the conditions in (a1) include a pressure in excess of 540 kPa-a.

6. The process of claim 1, wherein the reacting (a1) and dehydrating (b1) are conducted in the same reaction zone.

7. The process of claim 1, wherein the compound having the formula (I) comprises furan substituted at the 2- or 3- position.

8. The process of claim 1, wherein where $R^1$ is —$CH_3$ or CHO.

9. The process of claim 1, wherein the compound having the formula (II) comprises styrene or a substituted styrene and the compound of formula (IV) is a biphenyl compound.

10. The process of claim 1, wherein the compound having the formula (II) comprises para-methylstyrene.

11. The process of claim 1, wherein the compound having the formula (II) comprises vinylcyclohexane, vinylcyclohexene or a substituted analogue thereof.

12. The process of claim 11 and further comprising:
(c1) dehydrogenating the compound of formula (IV) to produce a biphenyl compound.

13. A process for producing a biphenyl compound, the process comprising:
(a2) reacting furan or a substituted furan compound having the formula (I):

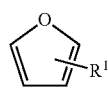

(I)

where $R^1$ is —H, —$CH_3$, —CHO, —$CH_2OH$, —COOH or —$COOR^2$ and $R^2$ is an alkyl group having from 1 to 20 carbon atoms with a compound having the formula (II):

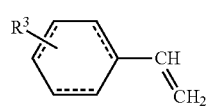

(II)

where $R^3$ is —H, —$NO_2$, —$CH_3$, —CHO, —$CH_2OH$, —COOH or —$COOR^4$ and $R^4$ is an alkyl group having from 1 to 20 carbon atoms under alkylation conditions effective to produce a compound having the formula (V):

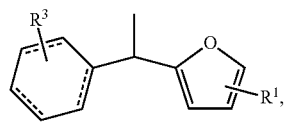

(V)

(b2) reacting at least part of the compound of formula (V) with ethylene under cycloaddition reaction conditions to produce a compound having the formula (VI):

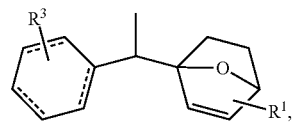

(VI)

and
(c2) dehydrating the compound of formula (VI) to produce a compound of formula (VII):

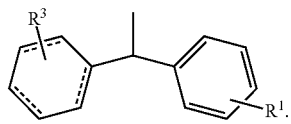

(VII)

14. The process of claim 1, wherein the reacting step (a2) is conducted in the presence of a catalyst.

15. The process of claim 14, wherein the catalyst comprises an acidic molecular sieve or a Lewis acid.

16. The process of claim 13, wherein the conditions in (a2) include a temperature from about 100° C. to about 400° C.

17. The process of claim 13, wherein the conditions in (a2) include a pressure of 270 to 540 kPa-a.

18. The process of claim 13, wherein the compound having the formula (I) comprises furan substituted at the 2- or 3- position.

19. The process of claim 13, wherein where $R^1$ is —$CH_3$ or —CHO.

20. The process of claim 13, wherein the compound having the formula (II) comprises styrene or a substituted styrene and the compound of formula (VII) is a biphenyl compound.

21. The process of claim 13, wherein the compound having the formula (II) comprises para-methylstyrene.

22. The process of claim 13, wherein the compound having the formula (II) comprises vinylcyclohexane, vinylcyclohexene or a substituted analogue thereof.

23. The process of claim 13 and further comprising:
(d2) dehydrogenating the compound of formula (VII) to produce a diphenyl compound.

* * * * *